(12) United States Patent
Lefkovitz

(10) Patent No.: US 8,684,958 B1
(45) Date of Patent: Apr. 1, 2014

(54) CERVICAL TRACTION/STRETCH DEVICE

(75) Inventor: Joshua A. Lefkovitz, Chicago, IL (US)

(73) Assignee: Zing Anything LLC, Akron, OH (US)

( * ) Notice: Subject to any disclaimer, the term of this patent is extended or adjusted under 35 U.S.C. 154(b) by 205 days.

(21) Appl. No.: 13/362,375

(22) Filed: Jan. 31, 2012

Related U.S. Application Data

(60) Provisional application No. 61/437,736, filed on Jan. 31, 2011.

(51) Int. Cl.
*A61F 5/00* (2006.01)
*A61F 5/24* (2006.01)

(52) U.S. Cl.
USPC .......................................... 602/40; 128/97.1

(58) Field of Classification Search
USPC ................. 602/13, 17–18, 32, 40, 36, 61, 74; 128/869, 845–846, 857, 870, 97.1, 128/DIG. 23, DIG. 19, DIG. 20; 5/622, 5/636–637

See application file for complete search history.

(56) References Cited

U.S. PATENT DOCUMENTS

| | | | |
|---|---|---|---|
| 5,441,479 | A | 8/1995 | Chitwood |
| 5,454,781 | A | 10/1995 | Chitwood |
| 5,569,175 | A | 10/1996 | Chitwood |
| 5,916,185 | A | 6/1999 | Chitwood |
| 7,670,307 | B2 | 3/2010 | Chitwood et al. |
| 2010/0121243 | A1 | 5/2010 | Aune, Jr. et al. |

*Primary Examiner* — Patricia Bianco
*Assistant Examiner* — Ophelia A Hawthorne
(74) *Attorney, Agent, or Firm* — John D. Gugliotta

(57) ABSTRACT

A cervical traction device is provided that is made of high density foam that cradles the users head and neck while providing adjustable traction to the user. The innovation lies in the air pump adjustable "lift" bladder that creates the adjustable incline traction.

7 Claims, 9 Drawing Sheets

CERVICAL TRACTION/STRETCH DEVICE

RELATED APPLICATIONS

The present invention claims the benefit of U.S. Provisional Application 61/437,736 filed on Jan. 31, 2011.

BACKGROUND OF THE INVENTION

1. Technical Field of the Invention

The present invention relates to cervical traction and stretch devices of the type positioned under the neck of a user lying on a flat surface.

2. Description of the Background Art

Conventional cervical traction and stretch devices are generally positioned between the shoulders and the head of the user, and includes an expandable, inflatable elastic body. The expansion occurs through the inflation of a bellows between the head and shoulders. A hand operated bulb type air pump with a manually operated air pressure relief valve is connected to the inflatable body, causing inflation and deflation of the bellows. Expansion and contraction of the bellows increases and releases the stretching force on the neck.

In such devices, compromises are made to solve some of the problems and limitations encountered in their use. These can include: portability; comfort; convenience of installation, removal and wear; adjustability of pressure (with a range of up to about 30 psi); exertion of limited or no pressure on the temporomandibular joint; and adjustability to fit any sized user.

According to the present invention there is provided a cervical traction/stretch device comprising a pair of hollow inflatable bellows made of an elastically expandable material and positioned along different planes of use. High density foam cradles are adapted for securing the users head and neck, with a first inflation bladder along a vertical plane providing adjustable traction to the user. An air pump adjustable "lift" bladder in a horizontal plane creates adjustable incline traction.

The present invention accomplishes the application of situational neck traction and inclined traction in a portable, comfortable and convenient pre-assembled device that is adaptable to any sized user (via adjustable inserts) and offers over 30 lbs of adjustable pressure while exerting no pressure on the temporomandibular joint.

SUMMARY OF THE INVENTION

1. Description of the Preferred Embodiment

The present invention is a new type of cervical traction system that provides an even decompression of the anterior and posterior cervical discs, while supporting the spinal curve. The present invention cradles the head and neck via a curvature in the neck portion of the device, as well as a special head rest section that is vertically inflatable. Creating a cushion for the user while in use, both of these areas inflate with over 30 lbs of adjustable pressure to create traction in the cervical curve that spaces the cervical vertebrae evenly. The lateral incline for the head is adjustable from 0 to 15 degrees by pumping up the headrest.

The traction applied is controlled by, the user through two hand pump controls. One controls the cervical "pull" and one controls the lateral "incline" of the device.

Custom inserts are used to size the patient to the device. Each device includes all three custom inserts so that the device can be sized to the user. The custom insert is made of low density soft foam, and will reduce or eliminate strain on the jaws temporomandibular joint (TMJ).

2. Advantageous Effects of Invention

The advantages of the present invention are intended for use with the follow conditions and indications: relieve pain; relax muscles; relieve soreness and joint stiffness; reduce inflammation; and, increase blood flow.

Further, a device incorporating the present teachings would be sufficiently portable, require no assembly, and exert over 30 lbs of adjustable pressure while exerting no pressure on the temporomandibular joint.

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
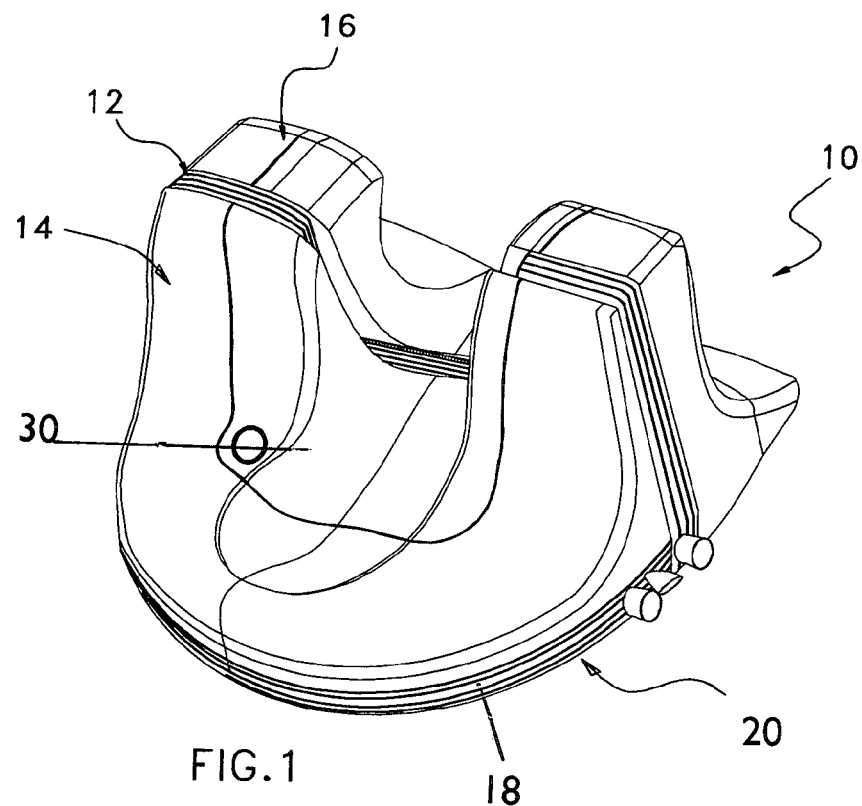
FIG. 1 is a front perspective view of a cervical traction/stretch device according to the preferred embodiment of the present invention.
Figure 2:
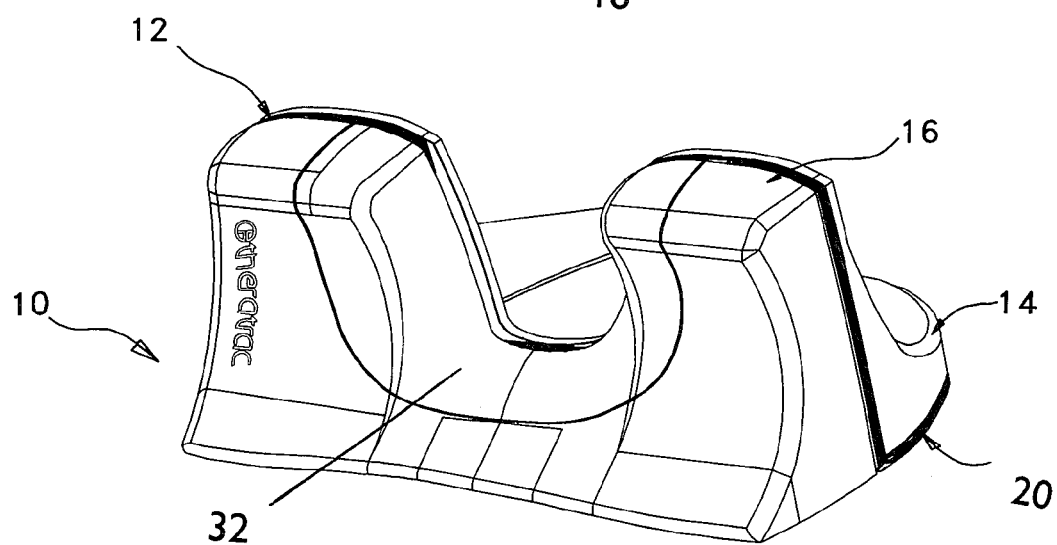
FIG. 2 is a rear perspective view thereof.
Figure 3:
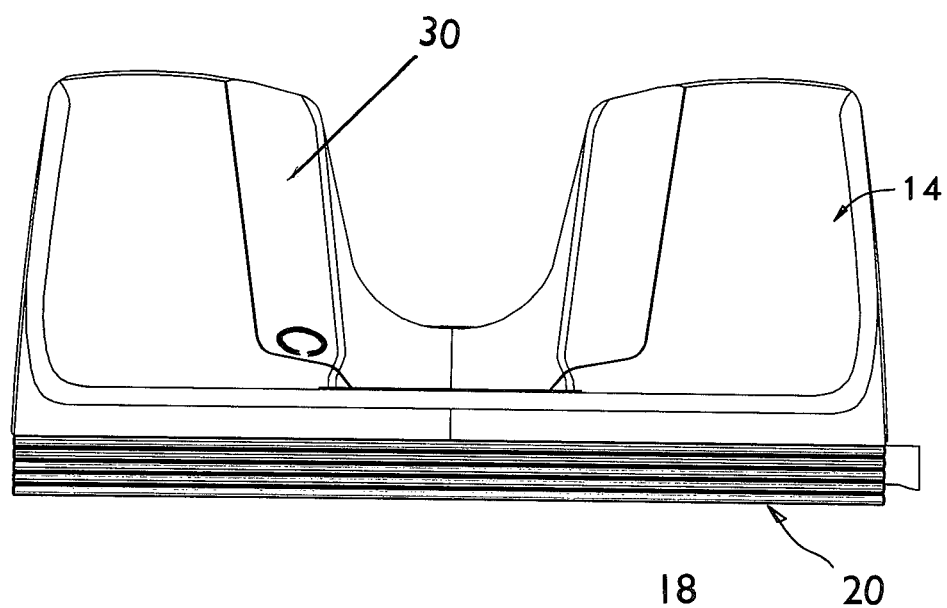
FIG. 3 is a distal elevational view thereof.
Figure 4:
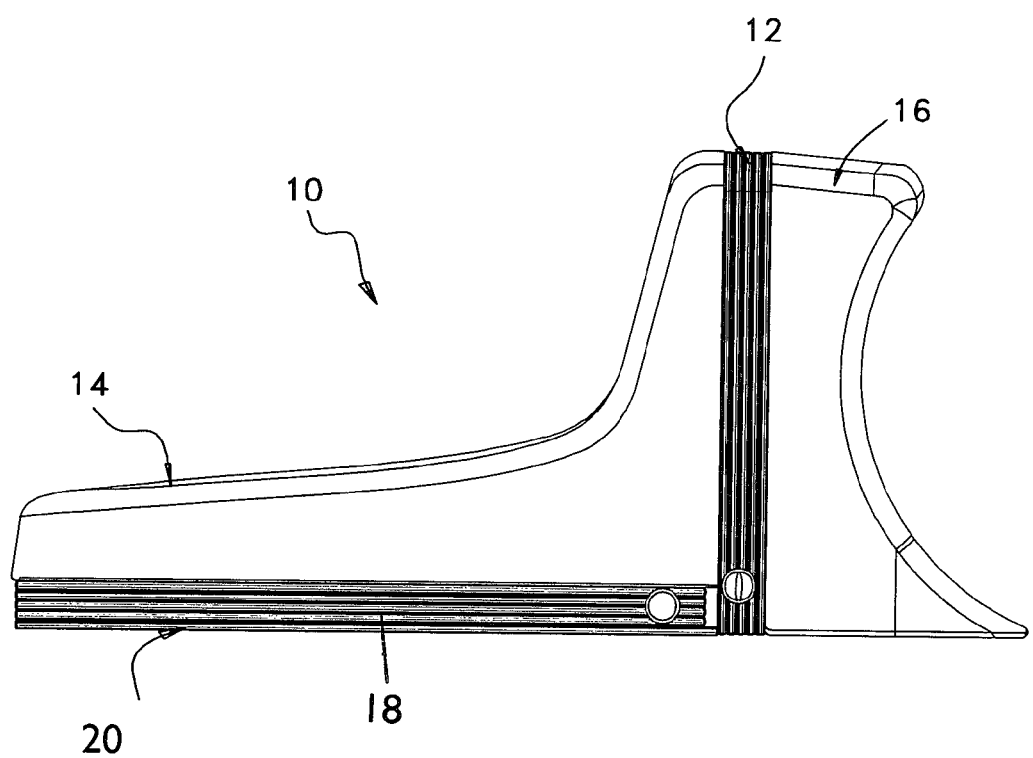
FIG. 4 is left side elevational view thereof.
Figure 5:
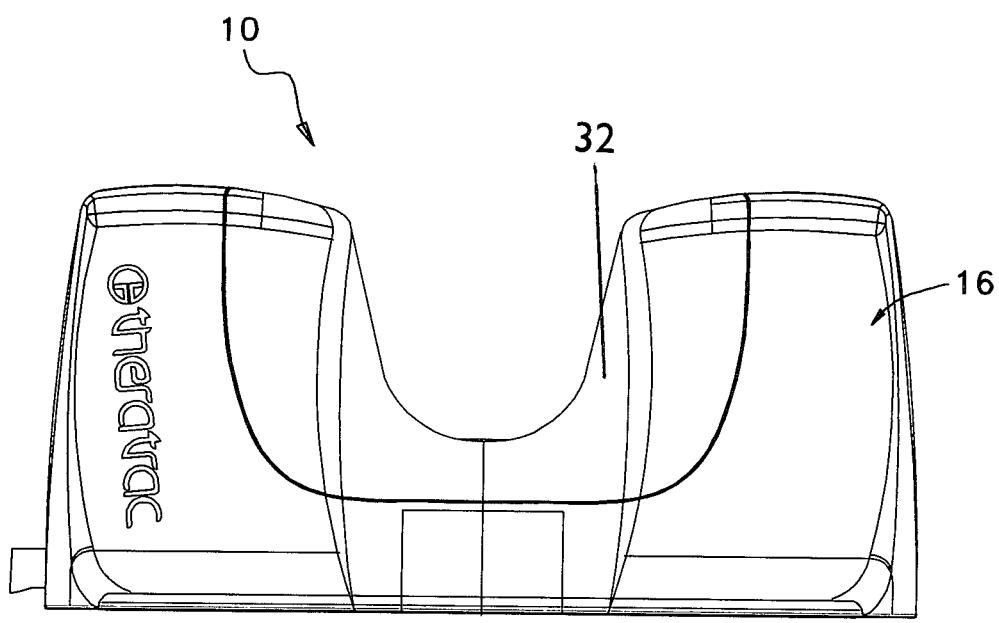
FIG. 5 is an axial elevational view thereof.
Figure 6:
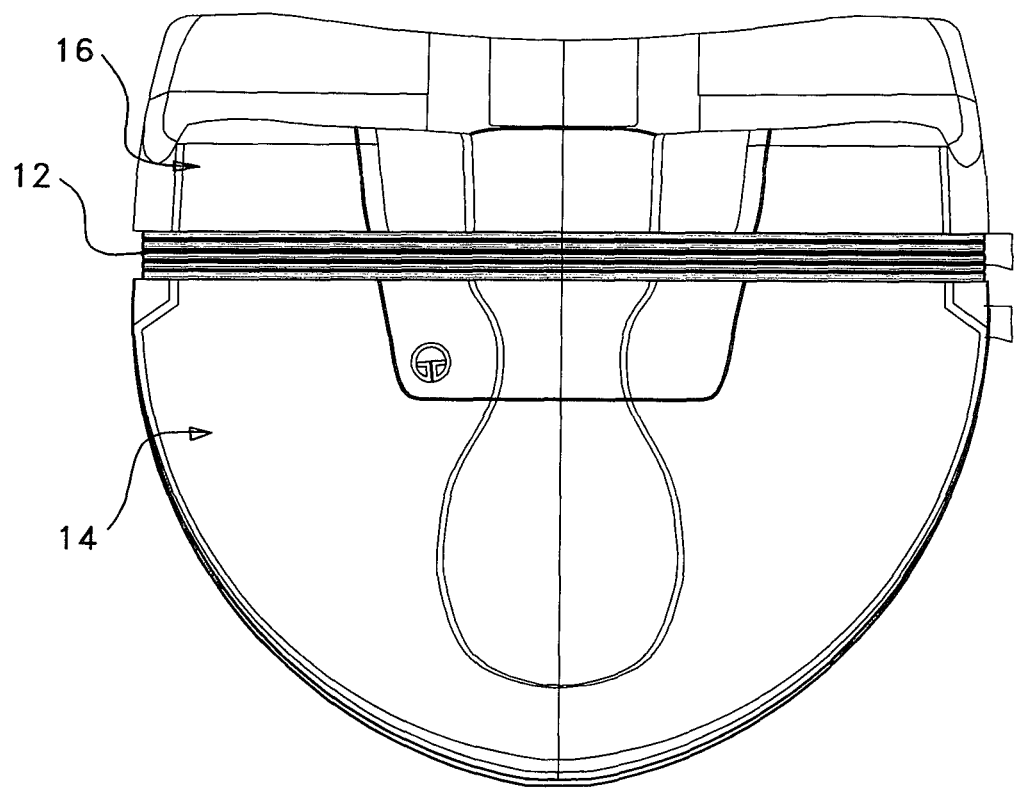
FIG. 6 is a top plan view thereof.
Figure 7:
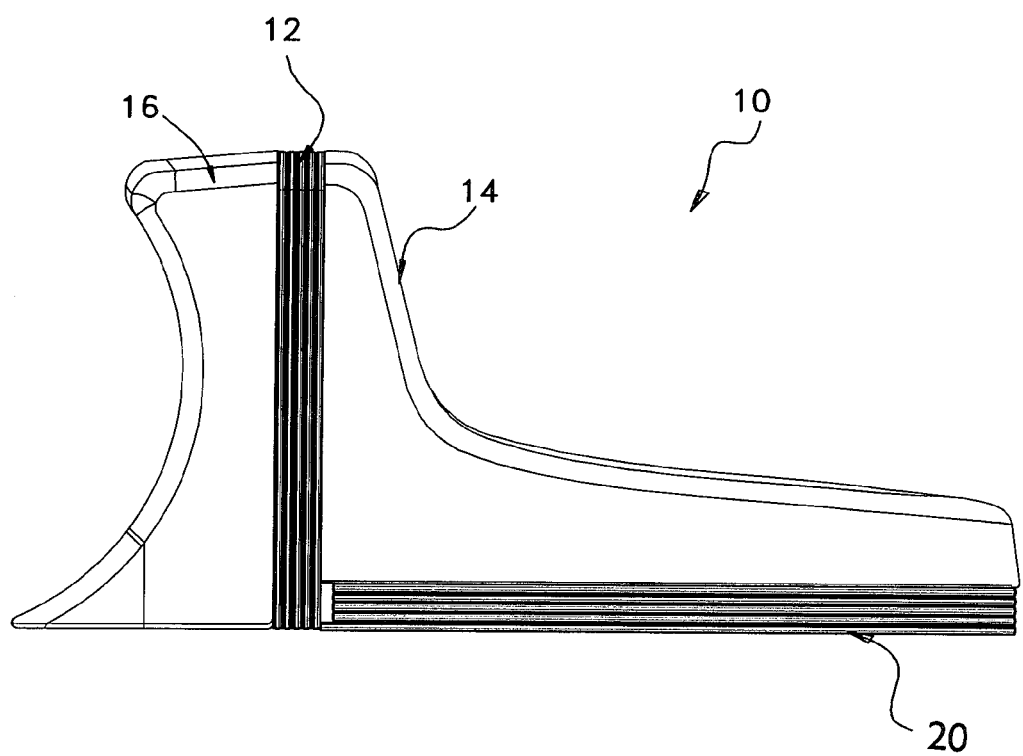
FIG. 7 is a right side elevational view thereof.
Figure 8:
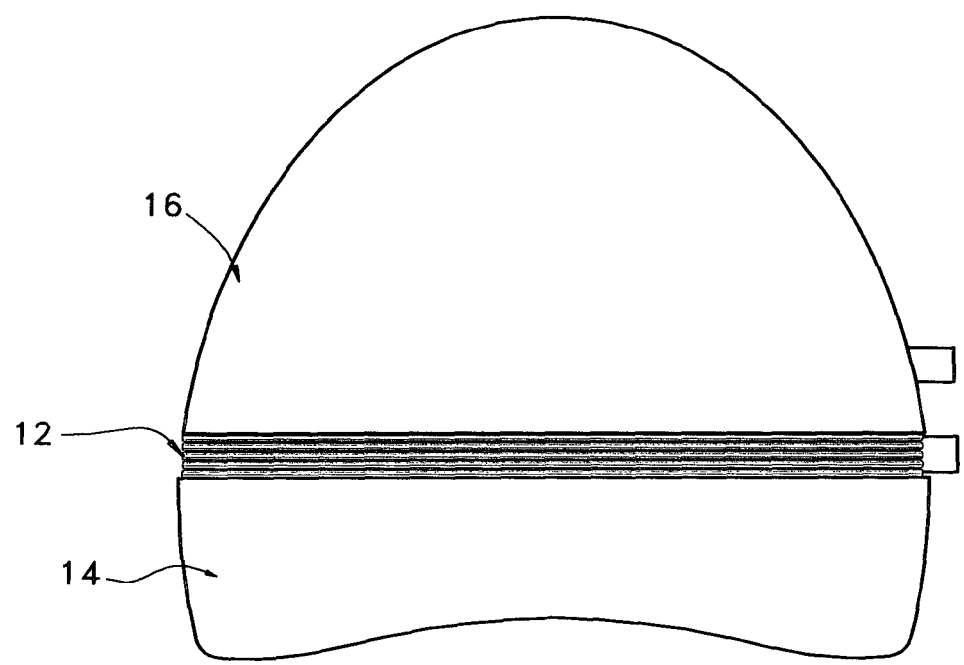
FIG. 8 is a bottom plan view thereof.
Figure 9:
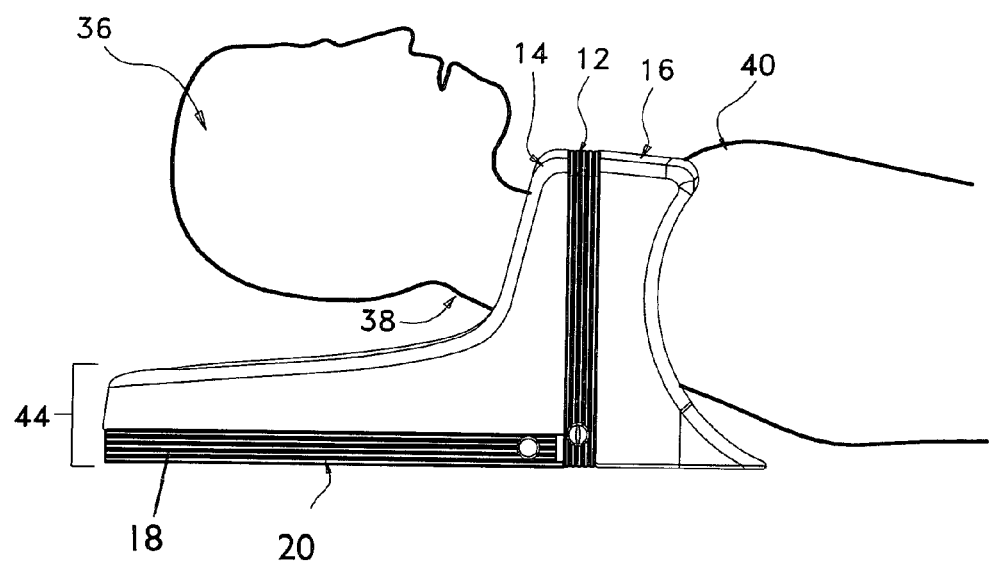
FIG. 9 is a right side elevational view of a cervical traction/stretch device according to the preferred embodiment of the present invention in use by a user.
Figure 10:
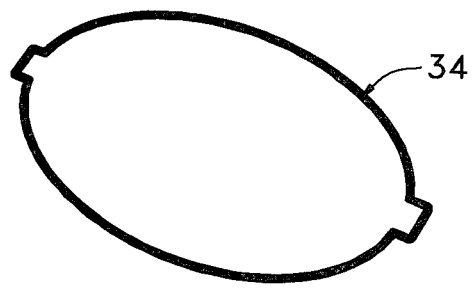
FIG. 10 is a front elevational view of a first air pump.
Figure 11:
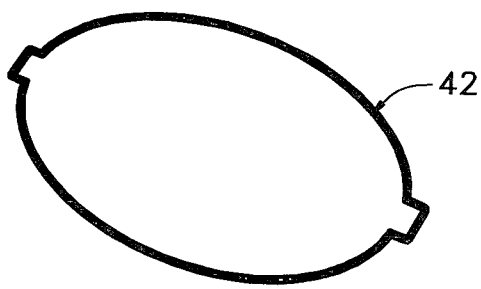
FIG. 11 is a front elevational view of a second air pump.

Referring now to the drawings in greater detail there is illustrated in FIG. 1 through FIG. 11, a cervical traction/stretch device 10 is shown constructed according to the teachings of the present invention. The device 10 is formed of a main bladder insert 12 that is oriented along a vertical plane and is bounded on a distal side by a main support 14 and on an axial side by a shoulder support 16. A lift bladder 18, oriented along a horizontal plane, is positioned beneath the main support 14 and above a horizontal support plate 20.

The main support 14 is made of high density foam that cradles the users head and neck while providing adjustable traction to the user. The main support 14 further comprises a main insert 30 that is removable and replaceable with various sized inserts 30 to allow for sizing the device to the patient using the included soft foam inserts.

Similarly, the shoulder support 16 is also made of high density foam that firmly abuts the upper portion of the shoulders of the user. The shoulder support 16 further comprises a shoulder insert 32 that is removable and replaceable with various sized inserts 32 to allow for sizing the device to the patient using the included soft foam inserts. The main bladder 12 is in fluid communication with an air pump 34 to allow for adjustable traction or "stretch" to be generated horizontally along the cervical vertebrae of the user between the head 36, neck 38 and shoulders 40. It is anticipated the first air pump 34 can control the expansion of the main bladder to between about 0-30 lbs of pressure can be gradually generated or released by the user. The lift bladder 18 is further in fluid communication with a second, similar air pump 42 to allow for adjustable "lift" to be created in the vertical plane. It is anticipated that through the use of the second hand pump, the user can control the outward expansion of the neck traction bladder to control the elevation and lift of the head rest. The "lift" creates incline traction adjustable creating a lateral incline 44 from 0 to 15 degrees.

As would be obvious to a person having ordinary skill in the relevant art, in light of the present teachings, it can be seen that the delivery and application of pneumatic pressure to the neck bladder or lift bladder can be accomplished in any number of ways without negatively impacting the teaching, benefits and improvements of the present invention. By way of example, and not as a limitation, the use of tubing connecting a bellows portion to an air pump can be used, as could be the use of a manually compressible bulb of the type known that has at its outer end a one way inlet valve which allows air to be sucked into the bulb, but does not allow air to flow out of the bulb when it is compressed.

2. Operation of the Preferred Embodiment

In operation, the present invention provides an even decompression of the anterior and posterior cervical discs, while supporting the spinal curve. The main support cradles the head and neck via a curvature in the neck portion of the device, as well as a special head rest section that is vertically inflatable. Creating a cushion for the user while in use, both of these areas inflate with over 30 lbs of adjustable pressure to create traction in the cervical curve that spaces the cervical vertebrae evenly. The lateral incline for the head is adjustable from 0 to 15 degrees by pumping up the headrest.

The traction applied is controlled by the user through two hand pump controls. One controls the cervical "pull" and one controls the lateral "incline" of the device.

Custom inserts are used to size the patient to the device. Each device includes all three custom inserts so that the device can be sized to the user. The custom insert is made of low density soft foam, and will reduce or eliminate strain on the jaws temporomandibular joint (TMJ).

The present invention is operated by first sizing the device to the patient using the included soft foam inserts. Next, the patient lies down and inserts their neck and head into the device. Through the use of two hand pumps, the user can control the outward expansion of the neck traction bladder. The present invention is adjustable from 0-30 lbs of pressure and the pressure can be released gradually by the user. The other hand pump controls the elevation and lift of the head rest. The "lift" creates an inclined traction adjustable from 0 to 15 degrees.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

Having thus described the invention what is claimed as new and desired to be secured by Letters Patent is as follows:

1. A cervical traction/stretch device comprising:
   a main bladder oriented along a vertical plane and is bounded on a distal side by a main support and on an axial side by a shoulder support;
   a lift bladder oriented along a horizontal plane and positioned beneath said main support and above a horizontal support plate;
   said main support further comprises a main soft foam insert that is removable and replaceable to allow for sizing said main support to a head and neck of a user using said main soft foam insert;
   said shoulder support is made of high density foam that firmly abuts a shoulder of said user;
   said shoulder support further comprising a shoulder insert that is removable and replaceable to allow for sizing said shoulder support to a shoulder of said user using said shoulder insert;
   wherein said main bladder is in fluid communication with a first air pump to allow for adjustable traction or "stretch" to be generated horizontally along a cervical vertebrae of said user between said head and said shoulder of said user; and
   wherein said lift bladder is further in fluid communication with a second air pump to allow for adjustable "lift" to be created in said vertical plane creating a lateral incline for said head of said user.

2. The cervical traction/stretch device of claim 1, wherein said main support is made of high density foam that cradles a head and a neck of said user while providing adjustable traction to said user.

3. The cervical traction/stretch device of claim 2, wherein said main soft foam insert is adaptable to different sizes to allow for sizing using said various different sizes of said main soft foam insert.

4. The cervical traction/stretch device of claim 1, wherein said shoulder support is made of high density foam that firmly abuts an upper portion of a shoulder of said user.

5. The cervical traction/stretch device of claim 4, wherein said shoulder insert is adaptable to different sizes to allow for sizing said device using said different sizes of said shoulder insert.

6. The cervical traction/stretch device of claim 1, wherein said first air pump releasably controls expansion of said main bladder to between approximately 0 to approximately 30 pounds of pressure.

7. The cervical traction/stretch device of claim 1, wherein said second air pump controls a second expansion of said lift bladder creating said lateral incline in the range of approximately 0 to approximately 15 degrees.

* * * * *